United States Patent [19]

Stein

[11] 4,371,539
[45] Feb. 1, 1983

[54] CNS STIMULANTS
[75] Inventor: Reinhardt P. Stein, Audubon, Pa.
[73] Assignee: American Home Products Corporation, New York, N.Y.
[21] Appl. No.: 257,827
[22] Filed: Apr. 27, 1981
[51] Int. Cl.$^3$ .................... C07D 271/04; A61K 31/42
[52] U.S. Cl. .................................... 424/272; 548/125
[58] Field of Search ......................... 548/125; 424/272

[56] References Cited
U.S. PATENT DOCUMENTS

| | | | |
|---|---|---|---|
| 3,312,690 | 4/1967 | Masuda et al. | 548/125 |
| 3,769,283 | 10/1973 | Masuda et al. | 548/125 |
| 3,812,128 | 5/1974 | Masuda et al. | 548/125 |
| 4,245,100 | 1/1981 | Kholodov et al. | 548/125 |
| 4,277,609 | 7/1981 | Stein | 548/125 |
| 4,289,885 | 9/1981 | Stein | 548/125 |
| 4,301,285 | 11/1981 | Stein | 548/125 |

FOREIGN PATENT DOCUMENTS

| | | | |
|---|---|---|---|
| 1942854 | 9/1970 | Fed. Rep. of Germany | 548/125 |
| 2028880 | 12/1971 | Fed. Rep. of Germany | 548/125 |

OTHER PUBLICATIONS

Mashkovskii et al; Chem. Abs., vol. 77:114435r, (1972).
Olovyanishnikova et al; Chem. Abs., vol. 84:30971u, (1976).

Primary Examiner—Mary C. Lee
Attorney, Agent, or Firm—Richard K. Jackson

[57] ABSTRACT

3-[Methyl(phenylmethyl)amino]-N-[(phenylamino)carbonyl]sydnone imine or a pharmaceutically acceptable salt thereof serve as central nervous system stimulants with much less sympathomimetic activity than is found in amphetamine like stimulants.

2 Claims, No Drawings

CNS STIMULANTS

BACKGROUND OF THE INVENTION

After the discovery of the central nervous system stimulatory properties of 3-(1-methyl-2-phenylethyl)-N-(phenylcarbamoyl)sydnone imine (Sydnocarb; U.S.S.R. 329,890 and Offenlegungsschrift 2,028,880) various analogues have been reported. U.S.S.R. 222,370 and Offenlegungsschrift 2,738,022 disclose sydnone imines which contain phenyl, 1- or 2-phenylethyl and the phenylisopropyl groups in 3-position as well as N-meta- and para-chlorophenyl and N-phenyl carbamoyl groups. Variations of 3-benzyl sydnonimines are disclosed in U.S. Pat. No. 3,277,108. Other variously substituted 3-aralkyl sydnonimines are disclosed by Olovyanishinkiva et al. Khim. Geterotsikl Soedin, 2 170–175 (1978) and 9 1198–1203 (1975).

Sydnocarb is conventionally produced by cyanomethylation of amphetamine followed by nitrosation and ring closure with a mineral acid to yield sydnophen as an acid halide salt which is reacted with phenylisocyanate under mildly basic conditions to introduce the N-phenylcarbamoyl group. As an asymmetric compound, amphetamine may be employed as the initial reactant as the racemic d,l-mixture or as the pure d- or l-isomer to yield racemic or optically active sydnophen and ultimately sydnocarb.

Yashunskii et al., J. Med. Chem., 14 1013–1015 (1971) disclose the marked CNS-stimulatory effect of 3-(1-methyl-2-phenylethyl) sydnonimine (Sydnophen). The relative activities of a large number of alkyl, aryl and aralkylsydnonimines are presented in Table 1 on page 1014. Most of them, including compound XVIII (2-hydroxy-1-methyl-2-phenylethyl-sydnonimine), were essentially inactive central nervous system stimulants relative to compound XIII (Sydnophen), demonstrating the criticality of the structure of the 3-substituent in the Sydnocarb series of compounds as far as CNS stimulatory activity is concerned. Thus, although the activity profile of Sydnocarb is not identical to that of amphetamine, or for that matter Sydnophen, CNS stimulatory activity is a common property of the initial reactant amphetamine, the intermediate Sydnophen and the final product Sydnocarb.

DESCRIPTION OF THE INVENTION

In accordance with this invention there is provided new central nervous system (CNS) stimulants possessing comparable stimulatory activity to Sydnocarb while exhibiting much less sympathomimetic activity than norepinephrine, amphetamine, methamphetamine, l-Sydnocarb, l-3-[2-[(diethylaminoacetyl)oxy]-2-phenylethyl]N-[(phenylamino)carbonyl]sydnone imine (Example 9, Ser. No. 193,042, filed Oct. 2, 1980) and dl-3-[2-(dimethylamino)-2-phenylethyl]-N-[(phenylamino)carbonyl]sydnone imine (Example 2, Ser. No. 193,043, filed Oct. 2, 1980, now U.S. Pat. No. 4,289,885).

The CNS stimulants of this invention are 3-[methyl(phenylmethyl)amino]-N-[(phenylamino)carbonyl]sydnone imine or pharmaceutically acceptable salts thereof. These compounds differ from Sydnocarb in that they do not have an asymmetric center and there is no need for resolution of optical isomers at any stage of synthesis to determine in which optical antipode lies the most desirable activity.

In addition, this invention provides a method for relief of anergia which comprises administering 3-[methyl(phenylmethyl)amino]-N-[(phenylamino)carbonyl]sydnone imine or a pharmaceutically acceptable salt thereof, to a warm blooded animal in need thereof, orally or parenterally, in an amount sufficient to stimulate the central nervous system.

The compounds of this invention are prepared by the following technique:

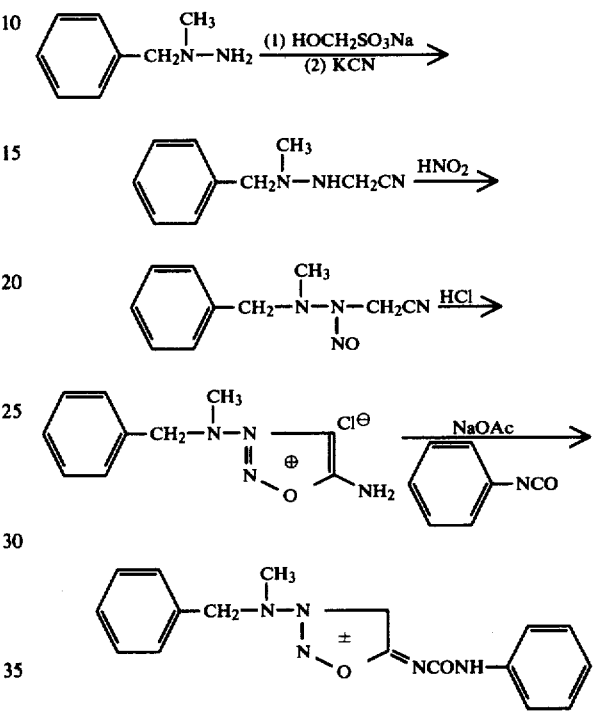

The starting material 1-benzyl-1-methylhydrazine is synthesized by the methods described by Butler et al., J. Med. Chem. 14 1052 (1971). The 1-benzyl-1-methylhydrazine is reacted with the sodium bisulfite formaldehyde addition product followed by reaction with a cyanide salt. The resulting cyanomethyl derivative is converted to the nitroso nitrile derivative with acidic nitrous acid and the nitrosonitrile derivative is converted to the oxadiazolium salt by treatment with anhydrous HCl. Neutralization of the oxadiazolium salt with a very mild base, such as sodium acetate, in the presence of an arylisocyanate affords the desired product. The pharmaceutically acceptable salts are prepared by conventional techniques from such organic or inorganic acid as hydrochloric, sulfuric, phosphoric, nitric, formic, acetic, propionic, oxalic, succinic, glycollic, lactic, malic, tartaric, citric, ascorbic, maleic, benzoic, salicylic, methane sulfonic, toluene sulfonic, and the like. The salts are employed in isolating the base in order to free it from reaction by-products. Due to the lability of the nitrosonitrile in the presence of base, direct conversion of the nitrosonitrile to the desired product in the presence of a base such as triethylamine is not as efficient as the stepwise conversion through the oxadiazolium salt (see Example 5, infra).

The CNS stimulant activity of the compounds of this invention was determined via the following standard test procedure:

Male mice weighing 17 to 25 gms. were injected orally with 3-[methyl(phenylmethyl)amino]-N-

[(phenylamino)carbonyl]sydnone imine, hydrochloride in 1% Tween ® 80. Control animals were injected with 1% Tween ® 80.

Six Columbus Instrument Company activity chambers were employed. Three mice given identical treatment were placed in each chamber for all tests. During each run, control animals (1% Tween ® only) occupy 3 chambers; the other 3 chambers measure activity of the drug treated animals. For each dose of drug the experiment was run two times in a counterbalanced design so that each specific activity chamber records the activity of control animals during one run, and the activity of drug animals on the other run. Thus at each dose level 18 mice were used in the drug group and 18 mice in the control group.

Activity counts were recorded every ten minutes for a period of 2 hours. The data was analyzed using Students "t" test comparing the means of the control and drug groups for each 10 minute period. The drug treated group was compared graphically with the control group in regard to duration of action and dose response at peak drug activity.

The product of Example 4 demonstrated 318 activity counts ($p<0.05$) at 10 mg/kg p.o. while dl-Sydnocarb demonstrates 636 activity counts ($p<0.01$) in the same test procedure.

The sympathomimetic activity of the product of Example 4, which is representative of the free base and other salts of this invention, was compared to representative CNS stimulants by administering the drugs to anesthetized, atropinized (1 mg/kg i.p.) pithed rats. The Sprague-Dawley rats, at least four in a test group, were normotensive males. The drugs were administered intravenously via a cannulated jugular vein and the blood pressure was measured from the carotid artery with a Statham Pressure Transducer monitored continuously on a Beckmann Multichannel Recorder. The mean blood pressure plus or minus standard error was determined as a measure of sympathomimetic activity. The values determined are as follows:

|  | mg/kg iv | mean B.P. |
|---|---|---|
| Norepinephrine | .0001 | +33 ± 3 |
|  | .001 | +82 ± 5 |
|  | .01 | +114 ± 6 |
| Amphetamine | .01 | +9 ± 1 |
|  | .1 | +33 ± 2 |
|  | 1.0 | +72 ± 1 |
| Methamphetamine | .01 | +10 ± 2 |
|  | .1 | +34 ± 2 |
|  | 1.0 | +63 ± 4 |
| L-Sydnocarb | .01 | +5 ± 1 |
|  | .1 | +6 ± 1 |
|  | 1.0 | +5 ± 2 |
|  | 10.0 | +32 ± 6 |
| Example 4 | .01 | +3 ± 1 |
|  | .1 | +4 ± 2 |
|  | 1.0 | +3 ± 2 |
|  | 10.0 | +13 ± 5 |
| Example 2 | .01 | +10 ± 3 |
| S.N. 193,043 | .1 | +7 ± 2 |
|  | 1.0 | +8 ± 1 |
|  | 10.0 | +49 ± 3 |
| Example 9 | .01 | +6 ± 1 |
| S.N. 193,042 | .1 | +6 ± 2 |
|  | 1.0 | +10 ± 2 |
|  | 10.0 | +45 ± 5 |

Thus the compounds of this invention exemplified by the product of Example 4 provide central nervous system stimulation with considerably less sympathomimetic activity than is found in known CNS stimulants such as amphetamine. The undesirable hypertensive side effect of amphetamines is not a problem with the compounds of this invention and they may be used to treat anergic patients suffering from hypertension without aggrevation of the latter problem.

As central nervous system stimulants with a unique activity profile, the compounds of this invention are useful in the treatment of anergic disorders (such as sleepiness and fatigue) including related types of depression and narcolepsy. Based upon the potency of the compounds of this invention in use in mice, the dose contemplated for use in the 70 kilogram human would vary from about 0.5 to 2 grams administered orally once or twice per day under the guidance of a physician. Of course, the dosage regimen as well as the route of administration, oral or parenteral, will vary with the condition of the patient relative to age, severity of depression, etc.

The following examples illustrate the preparation of the compounds of this invention employing 1-benzyl-1-methylhydrazine hydrochloride as the initial reactant (neutralized in situ with sodium bicarbonate) (Example 1), employing 1-benzyl-1-methylhydrazine as the free base (Example 2) and conversion of the oxadiazolium halide to the desired product (Example 3) and its hydrohalide salt (Example 4) as well as the less preferred direct conversion of the nitroso-nitrile with triethylamine and phenylisocyanate to the desired product (Example 5).

EXAMPLE 1

5-Amino-3-[methyl(phenylmethyl)amino]-1,2,3-oxadiazolium chloride

Dissolve 1-benzyl-1-methylhydrazine hydrochloride (23.2 g) in water (150 ml). If any neutral material remains out of solution remove it by extraction into diethyl ether. Stir the aqueous layer and add solid sodium bicarbonate (12.4 g) portionwise at a rate to prevent excessive foaming. After complete addition, stir, then add the sodium bisulfite addition product of formaldehyde (23.0 g) portionwise. Stir 15 minutes, then add potassium cyanide (13.0 g) and heat the reaction on the steam bath for 5 hours. Let the reaction stand at room temperature overnight. Extract the reaction well with diethyl ether, then wash, dry and evaporate the ether in vacuo. Pump the oil to dryness, then treat the oil in diethyl ether with decolorizing charcoal, filter and evaporate the ether in vacuo to obtain 19.8 g of 1-benzyl-2-cyanomethyl-1-methylhydrazine as a yellow oil. Cover the oil (19.5 g) with water (200 ml), stir and cool with an ice bath, then drip in 5 N aqueous HCl (45 ml). Cool the solution further with an ice-salt bath, then with stirring drip in a solution of sodium nitrite (15.4 g) in water (100 ml). Quickly extract the reaction with methylene chloride, then wash the extract with brine and dry the extract over anhydrous sodium sulfate for one-half hour. Filter and treat the filtrate with 5 N isopropanolic-HCl (45 ml), then allow to stand overnight. Evaporate the solvents in vacuo, add acetone and let stand to crystallize. Cool and filter to obtain 6.40 g. of the crude title product; m.p. 150°-153° C. (dec.).

Obtain an analytical sample from acetone; m.p. 155°-157.5° C. (dec.).

Analysis for: $C_{10}H_{13}ClN_4O$. Calculated: C, 49.90; H, 5.44; N, 23,28; Cl, 14.73%. Found: C, 49.40; H, 5.34; N, 22.51; Cl, 14.85%.

EXAMPLE 2

5-Amino-3-[methyl(phenylmethyl)amino]-1,2,3-oxadiazolium chloride

Cover the oily free base, 1-benzyl-1-methylhydrazine (47.5 g) with water (400 ml) and with stirring add the sodium bisulfite addition product of formaldehyde (50.0 g) and warm the mixture on the steam bath for ½ hour. Cool and add potassium cyanide (25.0 g), stir, then heat the reaction on the steam bath for 5 hours. Let the reaction cool and stand at room temperature overnight. Extract well with diethyl ether, then wash the extract with brine and dry, evaporate the ether in vacuo and pump to dryness to obtain 54.5 g of 1-benzyl-2-cyanomethyl-1-methylhydrazine as a yellow oil. Cover the oil with water (300 ml), stir and cool with an ice bath, then drip in 5 N aqueous HCl (125 ml). Stir, then filter through a glasswool plug to remove a small amount of neutral material. Cool the aqueous filtrate with an ice bath and with stirring drip in a solution of sodium nitrite (42.9 g) in water (200 ml). Stir for 15 minutes, then extract the reaction with methylene chloride. Dry the extract with anhydrous sodium sulfate for ½ hour. Filter and treat the filtrate with 5 N isopropanolic HCl (125 ml) and allow to stand overnight at room temperature. Evaporate the solvents in vacuo, add acetone, then cool and filter to obtain 15.4 g of the title product; m.p. 154°-156° C. (dec.).

EXAMPLE 3

3-[Methyl(phenylmethyl)amino]-N-[(phenylamino)carbonyl]sydnone imine

Stir 5-amino-3-[methyl(phenylmethyl)amino]-1,2,3-oxadiazolium chloride (3.61 g) with isopropanol (30 ml), cool with an ice bath, then add anhydrous sodium acetate (1.48 g), stir, then add phenylisocyanate (1.95 ml) and continue stirring at room temperature for 2 hours. Let stand overnight, then filter and air dry the resulting solid. Cover the solid with water (75 ml) and stir at room temperature for 2 hours. Filter and dry to obtain the free base form of the title product (3.95 g); m.p. 127.5°-129.0° C.

Obtain a pure sample of the above solid by recrystallization from isopropanol to get m.p. 124.0°-125.5° C.

EXAMPLE 4

3-[methyl(phenylmethyl)amino]-N-[(phenylamino)carbonyl]sydnone imine, hydrochloride Suspend the product of Example 3 (3.79 g) in ethyl acetate, add 5 N-isopropanolic HCl (3 ml) and swirl until conversion to the hydrochloride is complete to obtain 4.22 g of the title product; m.p. 168.5°-169.0° C. (dec.).

EXAMPLE 5

3-[Methyl(phenylmethyl)amino]-N-[(phenylamino)carbonyl]sydnone imine, hydrochloride Dissolve 1-benzyl-1-methylhydrazine hydrochloride (10.0 g) in water (40 ml), stir and cool with an ice bath, then add 37% formaldehyde solution (8.1 g). Continue cooling and stirring for 40 minutes, then drip in a solution of potassium cyanide (3.0 g) in water (40 ml). Stir for 3 hours, then extract the reaction with methylene chloride. Wash, dry and evaporate the extract in vacuo to obtain 8.1 g of 1-benzyl-2-cyanomethyl-1-methyl hydrazine. Cover the product with water (40 ml), cool with an ice bath, then carefully add concentrated aqueous-HCl (7.8 ml) dropwise. Further cool the reaction with an ice-salt bath, then drip in a solution of sodium nitrite (6.3 g) in water (50 ml) with continued stirring. After completing the addition, stir cold for 1½ hours. Extract the reaction with methylene chloride, then wash, dry and evaporate the solvent in vacuo to obtain the crude 1-benzyl-2-cyanomethyl-1-methyl-2-nitrosohydrazine (9.4 g). Dissolve the oil in dry toluene (50 ml), add phenylisocyanate (7.04 g), stir, then add triethylamine (4.7 g) and heat the reaction at 50°-60° C. for 6½ hours. Cool, filter and evaporate the solvents in vacuo, then pump dry to obtain 13.8 g of crude residue. Dissolve the product in ethyl acetate, add 5 N isopropanolic-HCl (17.2 ml). Scratch and stir, then let stand to crystallize. Filter to obtain 1.62 g of crude title product; m.p. 165° C. (dec.). Dissolve the solid in methylene chloride-methanol, treat with decolorizing carbon, filter then evaporate to low volume in vacuo. Add 95% ethanol and let stand to crystallize. Filter and dry to obtain 974 mg of the pure title product; m.p. 169° C. (dec.).

Analysis for: $C_{17}H_{17}N_5O_2 \cdot HCl$. Calculated: C, 56.74; H, 5.04; N, 19.46; Cl, 9.85%. Found: C, 56.45; H, 5.11; N, 19.90; Cl, 9.78%.

What is claimed is:

1. The compound which is 3-[Methyl(phenylmethyl)amino]-N-[(phenylamino)carbonyl]sydnone imine or a pharmaceutically acceptable salt thereof.

2. A method for treating anergia which comprises administering 3-[methyl(phenylmethyl)amino]-N-[(phenylamino)carbonyl]sydnone imine or a pharmaceutically acceptable salt thereof, to a warm blooded animal in need thereof, orally or parenterally, in an amount sufficient to stimulate the central nervous system.

* * * * *